United States Patent
Getts et al.

(10) Patent No.: US 9,689,036 B2
(45) Date of Patent: Jun. 27, 2017

(54) MIRNA BIOMARKERS FOR ULCERATIVE COLITIS

(75) Inventors: Robert C. Getts, Collegeville, PA (US); Thomas D. Stamato, Medford, NJ (US); Radharani Duttagupta, Foster City, CA (US); Keith W. Jones, Sunnyvale, CA (US)

(73) Assignee: Genisphere, LLC, Hatfield, PA (US)

( * ) Notice: Subject to any disclaimer, the term of this patent is extended or adjusted under 35 U.S.C. 154(b) by 157 days.

(21) Appl. No.: 14/345,745

(22) PCT Filed: Sep. 14, 2012

(86) PCT No.: PCT/US2012/055345
§ 371 (c)(1),
(2), (4) Date: Sep. 23, 2014

(87) PCT Pub. No.: WO2013/043482
PCT Pub. Date: Mar. 28, 2013

(65) Prior Publication Data
US 2015/0031567 A1 Jan. 29, 2015

Related U.S. Application Data

(60) Provisional application No. 61/536,836, filed on Sep. 20, 2011.

(51) Int. Cl.
*C12Q 1/68* (2006.01)

(52) U.S. Cl.
CPC ..... *C12Q 1/6883* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2011/0117111 A1   5/2011   Kwon et al.

OTHER PUBLICATIONS

PCT International Preliminary Report on Patentability in PCT/US2012/055345, mailed Apr. 3, 2014, 8 pages.
Allawi, Hatim T., et al., Quantitation of microRNAs using a modified Invader assay, *RNA* vol. 10 2004, 1153-1161.
Chen, Caifu, et al., MicroRNA Quantitation by RT-PCR, *Applied Biosystems* 2005, 1 page.
Chen, Caifu, et al., Real-time quantification of microRNAs by stem-loop RT-PCR, *Nucleic Acids Research* vol. 33 No. 20 e179 2005, 9 pages.
Duttagupta, Radha, et al., Genome-Wide Maps of Circulating miRNA Biomarkers for Ulcerative Colitis, *PLoS ONE* vol. 7 Issue 2, e31241 Jan. 1, 2012, 13 pages.
Edelstein, Leonard C., et al., MicroRNAs in platelet production and activation, *Blood* vol. 117 No. 20 May 19, 2011, 5289-5296.
Iborra, Marisa, et al., Identification of Serum and Tissue Micro-RNA Expression Profiles in Different Stages of the Inflammatory Bowel Disease, *Gastroenterology*, vol. 140 No. 5 Suppl. 1, p. S273 Digestive Disease Week 2011, Chicago, IL, XP-002688467 May 2011, 2 pages.
Lunn, Marie-Louise, et al., MicroRNA quantification form a single cell by PCR using SYBR Green detection and LNA-based primers, *Nature Methods* Feb. 2008, 2 pages.
Luminex Assays, High-throughput Multiplex Bead Based Assays, QuantiGene Plex 2.0, *Panomics, Inc.* 2007, 12 pages.
Neely, Lori, A., et al., A single-molecule method for the quantitation of microRNA gene expression, *Nature Methods* vol. 3 No. 1 Jan. 2006, 41-46.
Persat, Alexandre, et al., Absolute Quantification of MicroRNA From Human and Mouse Tissue RNA Using Highly Selective Isotachophoretic Focusing, *14th International Conference on Miniaturized Systems for Chemistry and Life Sciences*, Oct. 3-7, 2010, Groningen, The Netherlands, 659-661.
Persat, Alexandre, et al., Quantification of Global MicroRNA Abundance by Selective Isotachophoresis, *Anal. Chem.* 2010, 5 pages.
TaqMan MicroRNA Assays Product Bulletin, *Applied Biosystems* 2006, 4 pages.
Wu, Feng, et al., Peripheral Blood MicroRNAs Distinguish Active Ulcerative Colitis and Crohn's Disease, *Inflamm. Bowel Dis.* vol. 17 No. 1 Jan. 1, 2011, 241-250.

*Primary Examiner* — Celine Qian
(74) *Attorney, Agent, or Firm* — Servilla Whitney LLC

(57) ABSTRACT

Methods for diagnosing inflammatory bowel disease and ulcerative colitis using miRNA biomarkers for these diseases are provided. Differential expression of the miRNA biomarkers in blood fractions, e.g., platelets, of diseased individuals as compared to expression levels in normal individuals indicates the presence of IBD or ulcerative colitis. Also provided are microarrays for use in the diagnostic methods, wherein the features of the microarray consist essentially of nucleic acid sequences that hybridize to the miRNA biomarkers and normalization controls.

6 Claims, 11 Drawing Sheets

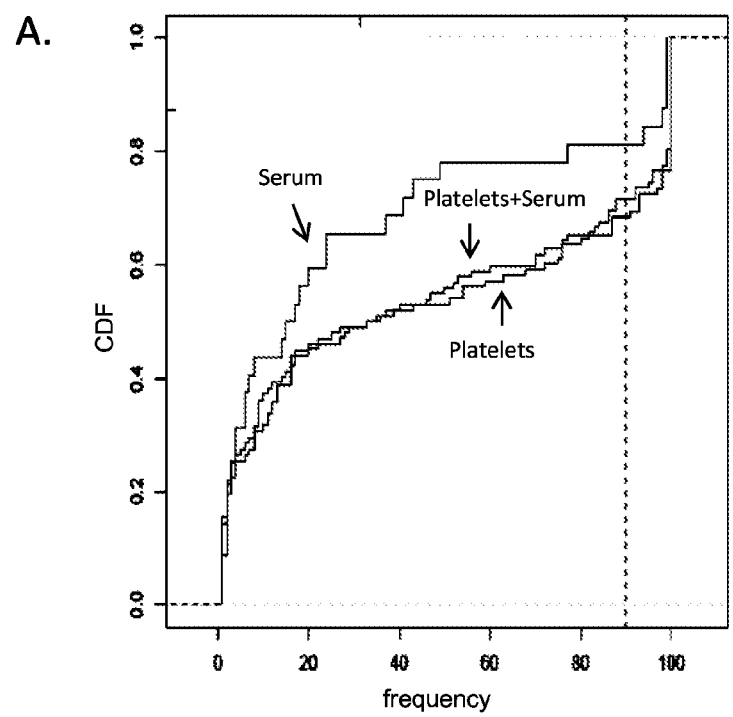
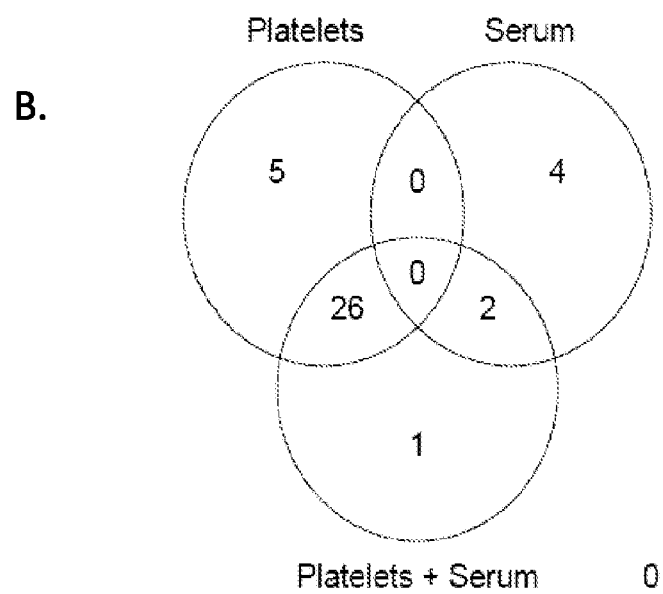
Fig. 2

Clusters of platelet miRNAs with correlated expression pattern (r > 0.600 and p < 0.0001)

| Clusters | miRNAs | Coefficient (r) | (p) | | miRNA | Chr | Position |
|---|---|---|---|---|---|---|---|
| Cluster 1: miR-378-star | miR-500 | 0.894426 | 7.55E-15 | | hsa-miR-500 | x | 49659779-49659862 |
| | miR-378 | 0.828918 | 3.97E-11 | | hsa-miR-378 | 5 | 149092581-149092646 |
| | miR-501-5p | 0.777506 | 3.61E-09 | | hsa-miR-501-5p | x | 49661070-49661153 |
| | miR-941 | 0.769904 | 6.35E-09 | | hsa-miR-941 | 20 | 62021238-62021326 |
| | miR-140-3p | 0.731856 | 8.06E-08 | 0.735839  4.26E-06 | hsa-miR-140-3p | 16 | 68524485-68524584 |
| | miR-422a | 0.699929 | 5.00E-07 | | hsa-miR-422a | 15 | 61950182-61950271 |
| | miR-720 | 0.651077 | 5.39E-06 | | hsa-miR-720 | 3 | 165541823-165541932 |
| | miR-27a-star | 0.722853 | 1.38E-07 | | hsa-miR-27a-star | 19 | 13808254-13808331 |
| | miR-181b | 0.683267 | 1.18E-06 | | hsa-miR-181b | 1,9 | 9:126495810-126495898 |
| | miR-31 | 0.732343 | 7.83E-08 | | hsa-miR-31 | 9 | 21502114-21502184 |
| | miR-150-star | 0.602149 | 3.95E-05 | | hsa-miR-150-star | 19 | 54695854-54695937 |
| Cluster 2: miR-146b-3p | miR-874 | 0.867578 | 4.35E-13 | 0.759595  2.63E-06 | hsa-miR-874 | 5 | 137011160-137011237 |
| | miR-138 | 0.651612 | 5.26E-06 | | hsa-miR-138 | 16,3 | 44130708-44130806 |
| Cluster 3: miR-188-5p | miR-769-5p | 0.878049 | 1.00E-13 | | hsa-miR-769-5p | 19 | 51214030-51214147 |
| | Let-7i-star | 0.807558 | 3.04E-10 | | hsa-let-7i-star | 12 | 61283733-61283816 |
| | miR-20b-star | 0.829967 | 3.56E-11 | | hsa-miR-20b-star | x | 133131505-133131573 |
| | miR-769-3p | 0.76319 | 1.03E-08 | 0.7663  2.14E-07 | hsa-miR-769-3p | 19 | 51214030-51214147 |
| | miR-550-star | 0.73584 | 6.31E-08 | | hsa-miR-550-star | 7 | 30295935-30296031 |
| | miR-1271 | 0.684895 | 1.09E-06 | | hsa-miR-1271 | 5 | 175727555-175727640 |
| | miR-22 | 0.701935 | 4.49E-07 | | hsa-miR-22 | 17 | 1563947-1564031 |
| | miR-1296 | 0.728963 | 9.61E-08 | | hsa-miR-1296 | 10 | 64802723-64802814 |
| Cluster 4: miR-362-5p | miR-532-5p | 0.917341 | 1.00E-16 | | hsa-miR-532-5p | x | 49654494-49654584 |
| | miR-345 | 0.760552 | 1.24E-08 | 0.780795  9.81E-07 | hsa-miR-345 | 14 | 99843949-99844046 |
| | miR-330-3p | 0.664491 | 2.93E-06 | | hsa-miR-330-3p | 19 | 50834092-50834185 |

Fig. 3

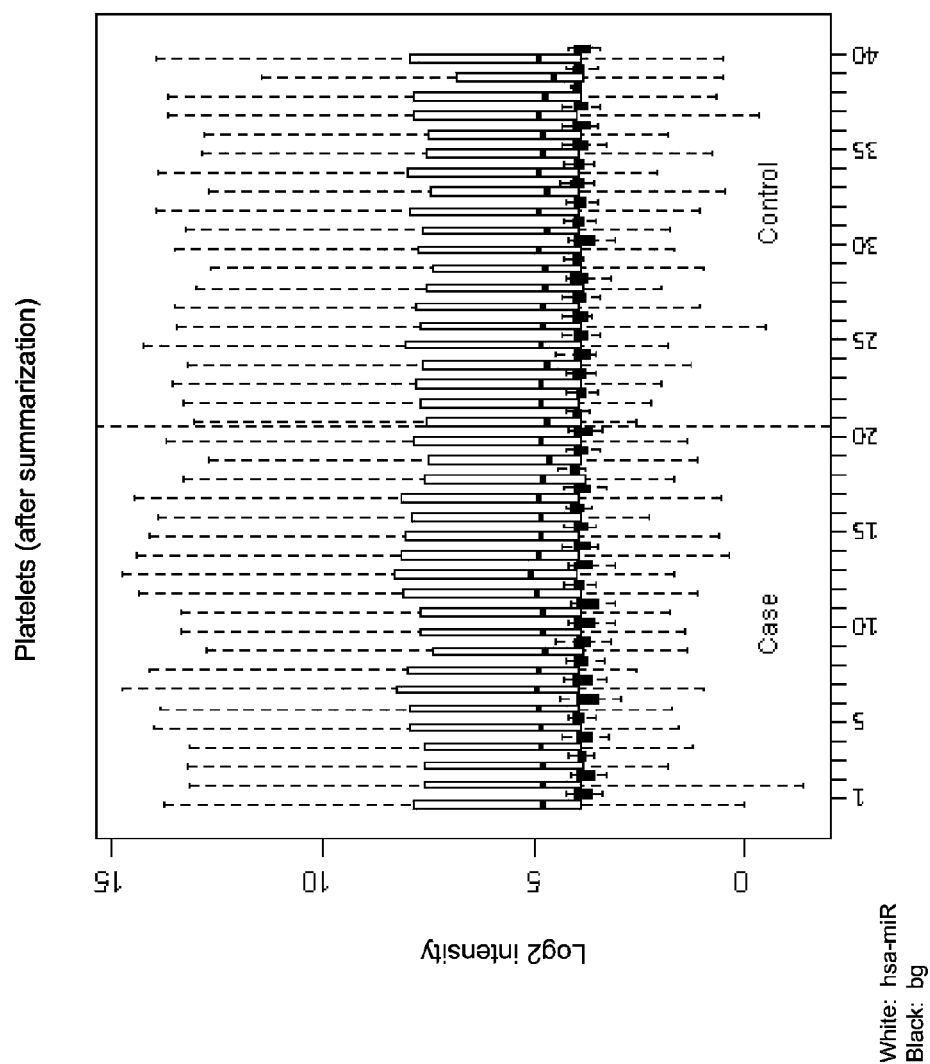

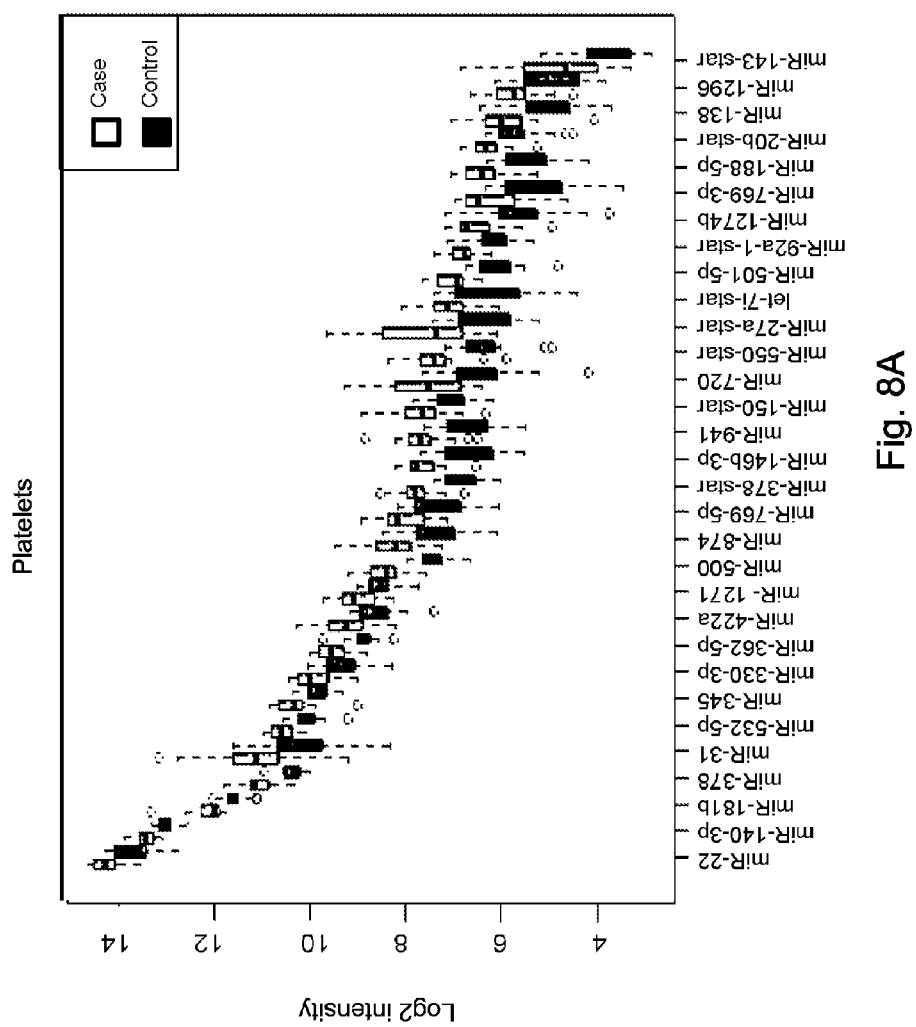

MIRNA BIOMARKERS FOR ULCERATIVE COLITIS

TECHNICAL FIELD

The present invention relates to biomarkers for diagnosis of inflammatory diseases and use of the biomarkers in diagnostic assay methods.

BACKGROUND

Inflammatory Bowel disease (IBD) is a chronic inflammatory disorder of the gastrointestinal tract that is comprised predominantly of Crohn's disease and ulcerative colitis. Both of these are debilitating inflammatory diseases characterized by inflammation of the digestive tract accompanied by severe diarrhea and abdominal pain leading to life-threatening complications. Crohn's disease involves inflammation of all layers of the bowel wall and any part of the gastrointestinal tract; with the most common sites being the small intestine, colon, and stomach. In contrast, ulcerative colitis is characterized by chronic inflammation of the colon but does not involve the small intestine. Currently, invasive procedures are used to confirm a diagnosis of IBD. These procedures involve endoscopy and clinical history. In order to obtain quantitative information on disease activity (as opposed to relying on subjective patient measurements) and to avoid invasive imaging procedures, there has been an active effort to identify serum/plasma microvesicle biomarkers that are indicative of disease subtype and inflammatory activity.

Pathogenesis of IBD involves interactions between both the innate and the adaptive immune system. Recent evidence suggests that these inflammatory systems can be influenced by both immune and non-immune cells. Platelets are non-immune, anuclear cells that affect blood hemostatis. Platelets also play an active role in a variety of inflammatory processes and platelet activation has been associated with chronic inflammatory coronary syndromes and autoimmune disease such as rheumatoid arthritis and systemic lupus erythematosus. Increased numbers of platelets have been seen in both Crohn's disease and ulcerative colitis. Upon activation, these platelets secrete pro-inflammatory cytokines that activate the same cellular and molecular pathways utilized by immune cells participating in an IDB episode. For instance, activated platelets release the potent chemokine RANTES, which is retained by endothelial cells and used to mediate adhesion of T cells to these cells. This cascade provides a link between platelet activation and T cell recruitment in IBD and suggests that platelets are involved in the cell-mediated enteric immune response.

microRNAs (miRNAs) are small, highly conserved non-coding RNAs that are thought to have a regulatory effect in a wide variety of eukaryotic organisms, including humans, plants and insects. Currently over 1000 mature miRNAs have been characterized in humans and it is believed that approximately 30% of all annotated human genes may potentially be targeted by miRNAs through post-transcriptional mechanisms including mRNA cleavage, inhibition of translation initiation, mRNA de-adenylation and/or sequestration of mRNA into P-bodies. miRNAs have been shown to play an integral role in immune response, cellular proliferation, apoptosis, metabolism, viral replication, stem cell differentiation and human development and are involved in the pathophysiology of autoimmune diseases and numerous cancers.

There is a significant need for identification of differentially expressed blood-based inflammatory biomarkers (or modulators of these inflammatory markers) that can be used for non-invasive diagnosis and therapeutic management of IBD. The present invention meets this need.

SUMMARY miRNA expression levels in microvesicles, peripheral blood mononuclear cells (PBMC) and platelets from individuals with ulcerative colitis and normal controls were evaluated. A set of 31 platelet-derived miRNAs that are differentially expressed between ulcerative colitis patients and normal controls was identified (referred to herein as the "Platelet Panel"). The platelet-derived miRNA signature has 92.8% accuracy, 96.2% specificity and 89.5% sensitivity in distinguishing IBD patients from normal individuals.

The Platelet Panel was validated with 88% accuracy through a QPCR based approach and 90% of the biomarkers were sub-stratified into 4 independent highly correlated clusters based on intensity distributions. Analysis of the spectrum of predicted targets of these biomarkers revealed an enrichment of pathways associated with cytoskeleton assembly, transcriptional regulation and activation of innate immune response pathways. Specifically, extensive overlap of miRNA targets with inflammatory cascades associated with ulcerative colitis such as TNF-alpha or T-cell activation was observed. Additionally, a correlation analysis of the miRNA targets and differently expressed mRNAs profiled from endothelial colonic tissues of ulcerative colitis patients revealed a statistically significant enrichment of anti-correlated targets in comparison to non-specific global down-regulation. In particular, at least 34% of the differentially down-regulated epithelial transcriptome was found to be suppressed by 17 out of the 31 platelet derived miRNA biomarkers.

BRIEF DESCRIPTION OF THE DRAWINGS

FIG. 2A is a graph illustrating the frequency of DE features occurring in the iterative derivation process. FIG. 2B illustrates the overlap between the different lists of biomarkers.

FIG. 3 shows the four correlation clusters of the miRNA biomarkers derived from platelets.

FIG. 6A shows quantile normalized data from the platelet fraction.

FIG. 8A is a graph illustrating the differentially expressed profiles and relative intensity of case and control samples for the platelet fraction.

DETAILED DESCRIPTION

Figure 1:
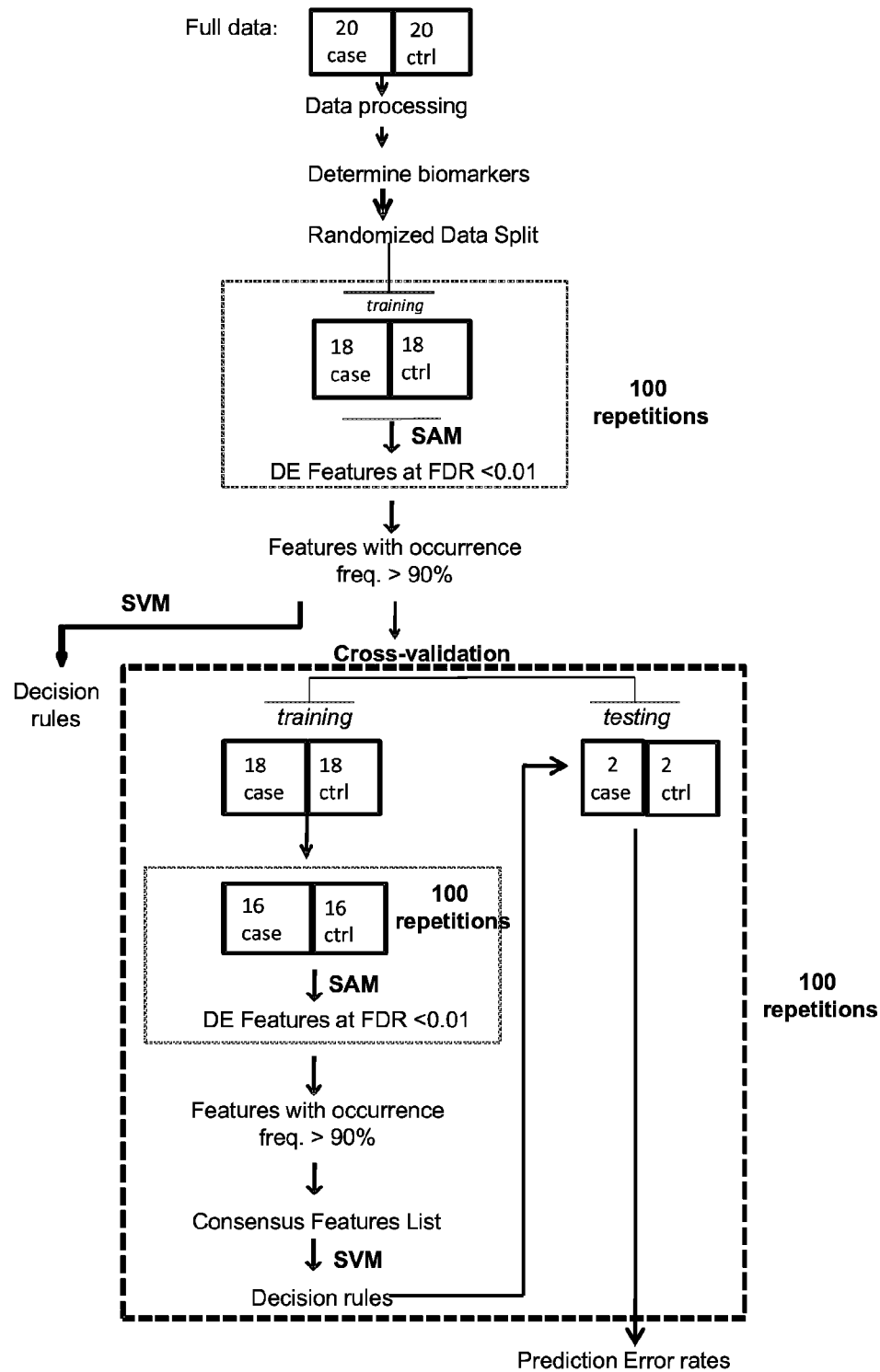
FIG. 1 illustrates the process for biomarker derivation from circulating miRNA profiles in different hematological fractions, and validation of the biomarkers.

Before describing several exemplary embodiments of the invention, it is to be understood that the invention is not limited to the details of construction or process steps set forth in the following description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

In a first embodiment, the invention provides a method for diagnosing ulcerative colitis comprising:
　a) quantifying individual miRNAs in a sample of platelet-derived miRNAs, wherein the quantified miRNAs are pl-hsa-let-7i-star_st, pl-hsa-miR-1271_st, pl-hsa-miR-1274b_st, pl-hsa-miR-1296_st, pl-hsa-miR-138_st, pl-hsa-miR-140-3p_st, pl-hsa-miR-143-star_st, pl-hsa-miR-146b-3p_st, pl-hsa-miR-150-star_st, pl-hsa-miR-181b_st, pl-hsa-miR-188-5p_st, pl-hsa-miR-20b-star_st, pl-hsa-miR-22_st, pl-hsa-miR-27a-star_st, pl-hsa-miR-31_st, pl-hsa-miR-330-3p_st, pl-hsa-miR-345_st, pl-hsa-miR-362-5p_st, pl-hsa-miR-378_st, pl-hsa-miR-378-star_st, pl-hsa-miR-422a_st, pl-hsa-miR-500_st, pl-hsa-miR-501-5p_st, pl-hsa-miR-532-5p_st, pl-hsa-miR-550-star_st, pl-hsa-miR-720_st, pl-hsa-miR-769-3p_st, pl-hsa-miR-769-5p_st, pl-hsa-miR-874_st, pl-hsa-miR-92a-1-star_st, and pl-hsa-miR-941_st;
　b) comparing the quantity of each quantified miRNA in the sample of platelet-derived miRNAs with a reference quantity representing normal expression levels of the miRNA; and
　c) identifying miRNAs which are differentially expressed in the platelet-derived miRNA sample compared to normal expression levels, wherein an increase in expression of at least 1.4-fold in each of the platelet-derived miRNAs compared to normal expression levels indicates ulcerative colitis.

In a second embodiment, the invention provides a method for diagnosing ulcerative colitis comprising:
　a) quantifying individual miRNAs in a sample of platelet—(pl) and serum/microvesicle—(sm) derived miRNAs, wherein the quantified miRNAs are pl-hsa-miR-1274b_st, pl-hsa-miR-138_st, pl-hsa-miR-140-3p_st, pl-hsa-miR-143-star_st, pl-hsa-miR-146b-3p_st, pl-hsa-miR-150-star_st, pl-hsa-miR-181b_st, pl-hsa-miR-188-5p_st, pl-hsa-miR-20b-star_st, pl-hsa-miR-22_st, pl-hsa-miR-27a-star_st, pl-hsa-miR-330-3p_st, pl-hsa-miR-362-5p_st, pl-hsa-miR-378_st, pl-hsa-miR-378-star_st, pl-hsa-miR-422a_st, pl-hsa-miR-423-3p_st, pl-hsa-miR-500_st, pl-hsa-miR-501-5p_st, pl-hsa-miR-532-5p_st, pl-hsa-miR-550-star_st, pl-hsa-miR-720_st, pl-hsa-miR-769-3p_st, pl-hsa-miR-769-5p_st, pl-hsa-miR-874_st, pl-hsa-miR-92a-1-star_st, pl-hsa-miR-941_st, sm-hsa-miR-1263_st, and sm-hsa-miR-202_st;
　b) comparing the quantity of each quantified miRNA in the sample of platelet- and microvesicle-derived miR-NAs with a reference quantity representing normal expression levels of the miRNA; and
　c) identifying miRNAs which are differentially expressed in the platelet- and microvesicle-derived miRNA sample compared to normal expression levels, wherein an increase in expression of at least 1.4-fold in each of the platelet- and microvesicle-derived miRNAs compared to normal expression levels indicates ulcerative colitis.

The foregoing methods for diagnosing ulcerative colitis may be performed by hybridization on a chip or microarray having the 31 platelet-derived miRNAs of the Platelet Panel or the 29 platelet- and microvesicle-derived miRNAs of the Platelet+Microvesicle Panel as features thereon. The quantity of an miRNA in the sample being tested is typically determined by measurement of the fluorescence intensity of hybridization to the corresponding feature.

Accordingly, in a third embodiment the invention provides microarrays for diagnosis of ulcerative colitis, wherein the features of the microarray consist essentially of the 31 platelet-derived miRNAs of the Platelet Panel and/or the 29 platelet- and microvesicle-derived miRNAs of the Platelet+Microvesicle Panel.

In a fourth embodiment, the invention provides methods for diagnosing inflammatory bowel disease comprising
　a) quantifying individual miRNAs in a sample derived from fractionated blood samples;
　b) comparing the quantity of each quantified miRNA in the sample with a reference quantity representing normal expression levels of the miRNA; and
　c) identifying miRNAs which are differentially expressed in the sample compared to normal expression levels, wherein an increase or decrease in expression of at least 1.4-fold in at least one miRNA compared to normal expression levels indicates IBD.

In the foregoing embodiment, the miRNA quantified may be one or more miRNAs selected from the group consisting of pl-hsa-let-7i-star_st, pl-hsa-miR-1271_st, pl-hsa-miR-1274b_st, pl-hsa-miR-1296_st, pl-hsa-miR-138_st, pl-hsa-miR-140-3p_st, pl-hsa-miR-143-star_st, pl-hsa-miR-146b-3p_st, pl-hsa-miR-150-star_st, pl-hsa-miR-181b_st, pl-hsa-miR-188-5p_st, pl-hsa-miR-20b-star_st, pl-hsa-miR-22_st, pl-hsa-miR-27a-star_st, pl-hsa-miR-31_st, pl-hsa-miR-330-3p_st, pl-hsa-miR-345_st, pl-hsa-miR-362-5p_st, pl-hsa-miR-378_st, pl-hsa-miR-378-star_st, pl-hsa-miR-422a_st, pl-hsa-miR-500_st, pl-hsa-miR-501-5p_st, pl-hsa-miR-532-5p_st, pl-hsa-miR-550-star_st, pl-hsa-miR-720_st, pl-hsa-miR-769-3p_st, pl-hsa-miR-769-5p_st, pl-hsa-miR-874_st, pl-hsa-miR-92a-1-star_st, and pl-hsa-miR-941_st and/or one or more miRNAs selected from the group consisting of pl-hsa-miR-1274b_st, pl-hsa-miR-138_st, pl-hsa-miR-140-3p_st, pl-hsa-miR-143-star_st, pl-hsa-miR-146b-3p_st, pl-hsa-miR-150-star_st, pl-hsa-miR-181b_st, pl-hsa-miR-188-5p_st, pl-hsa-miR-20b-star_st, pl-hsa-miR-22_st, pl-hsa-miR-27a-star_st, pl-hsa-miR-330-3p_st, pl-hsa-miR-362-5p_st, pl-hsa-miR-378_st, pl-hsa-miR-378-star_st, pl-hsa-miR-422a_st, pl-hsa-miR-423-3p_st, pl-hsa-miR-500_st, pl-hsa-miR-501-5p_st, pl-hsa-miR-532-5p_st, pl-hsa-miR-550-star_st, pl-hsa-miR-720_st, pl-hsa-miR-769-3p_st, pl-hsa-miR-769-5p_st, pl-hsa-miR-874_st, pl-hsa-miR-92a-1-star_st, pl-hsa-miR-941_st, sm-hsa-miR-1263_st, and sm-hsa-miR-202_st.

In addition to use of microarrays as discussed above, quantification of the relevant miRNAs in a sample may be performed using any method known in the art for quantification of miRNA or other small RNAs. All of the following methods are applicable to each of the embodiments described herein for diagnosing ulcerative colitis or inflammatory bowel disease. A first example of such methods is miRNA quantitation by RT-PCR using stem-loop primers for reverse transcription followed by real-time quantitative PCR using a TaqMan® probe. In this method, stem-loop reverse transcription (RT) primers are annealed to the miRNA targets and extended using reverse transcriptase. Generation of the cDNA is followed by real-time PCR with an miRNA-specific forward primer, a TaqMan probe, and a reverse primer. Quantities of the targeted miRNAs are estimated based on measurement of $C_T$ values. These methods are described, for example, by C. Chen, et al. Nucl. Acids Res., 2005, Vol. 33, No. 20, 9 pages, published online Nov. 27, 2005, and in publications and gene expression assay product bulletins of Applied Biosystems, Foster City, Calif.

Another example of an miRNA quantitation method for use in the embodiments of the invention is SYBR Green detection method using locked nucleic acid (LNA)-based primers (miRCURY™ LNA microRNA PCR system, Applied Biosystems, Foster City, Calif.; See M. Lunn, et al. Nature Methods, February 2008). In this method, miRNAs are reverse transcribed from total RNA in a sample using miRNA-specific RT primers, and the reverse-transcribed miRNAs are amplified using an LNA-enhanced PCR primer anchored in the miRNA sequence together and a universal PCR primer. Amplified miRNAs are quantitated by detection of fluorescence in the SYBR Green assay. Alternative LNA-based methods for quantitation of relevant miRNAs in the embodiments of the invention include the direct miRNA assay described by L. Neely, et al. Nature Methods, Vol. 3, No. 1, January 2006 (published online Dec. 20, 2005). In this method, two spectrally distinguishable fluorescent LNA-DNA oligonucleotide probes are hybridized to the miRNA of interest, and the tagged molecules are directly counted using single-molecule detection, such as laser-induced fluorescence (LIF) or fluorescence correlation spectroscopy.

Quantitation of miRNAs using a modification of the Invader assay initially developed for detection of mRNAs is described by H. Allawi, et al. (RNA (2004), 10:1153-1161), and is also applicable to the embodiments of the invention. In this assay, invasive and probe oligonucleotides are annealed to the miRNA target to form an overlap-flap structure that is a substrate for a structure-specific 5' nuclease (Cleavase). The non-complementary 5' flap of the probe is released by cleavage. In a secondary reaction to generate quantifiable signals, a secondary overlap-flap structure is formed by hybridizing both the released 5' flap and a FRET oligonucleotide to a secondary reaction template. Cleavage between the fluorophore and quencher of the FRET oligonucleotide produces a fluorescent signal which can be quantitated. A 2'-O-methyl arrestor oligonucleotide complementary to the probe sequesters any uncleaved probes so they cannot bind to the secondary reaction template. Because of the small size of miRNAs, the original mRNA assay was modified to include structures derived from the invasive and probe oligonucleotides in the primary reaction to form a dumbbell-like structure from the 5' flap is cleaved.

Another assay that can be used in the embodiments of the invention for quantitation of the relevant miRNAs is the Luminex® branched DNA (bDNA) assay (Panomics, Fremont, Calif.). This is a high-throughput multiplex bead-based assay based on the xMAP® technology of Luminex Corporation. Specific miRNAs are captured on their respective beads by hybridization with a capture probe, followed by sequential hybridization of pre-amplifier, amplifier and biotinylated label probes. Binding with streptavidin-conjugated phycoerythrin and analysis of individual beads for level of fluorescence quantifies the amount of miRNA captured by the bead. This assay is described in the Luminex product bulletins published by Panomics.

EXAMPLES

Figure 6B:
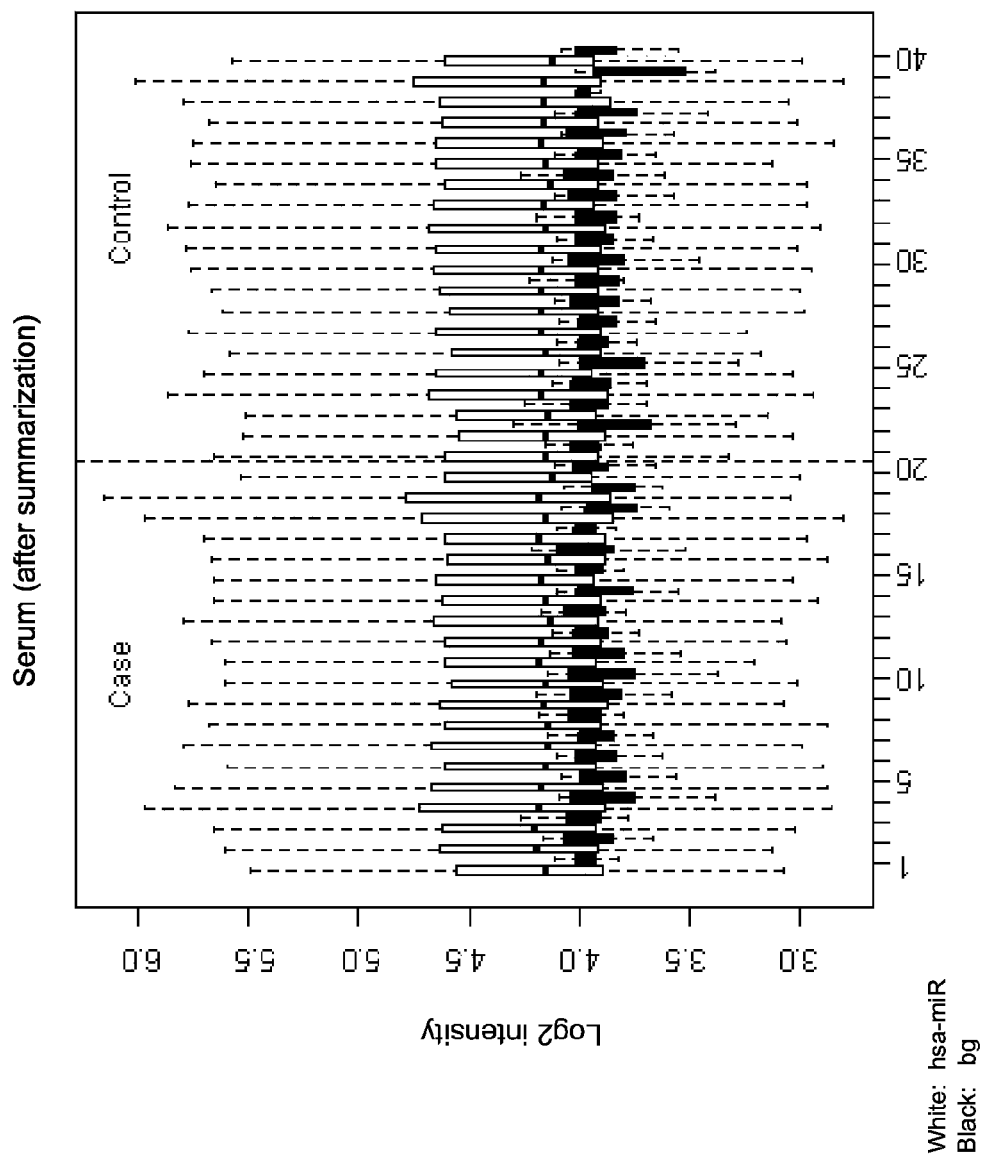
FIG. 6B shows quantile normalized data from the serum microvesicle (Serum) fraction.
Figure 6C:
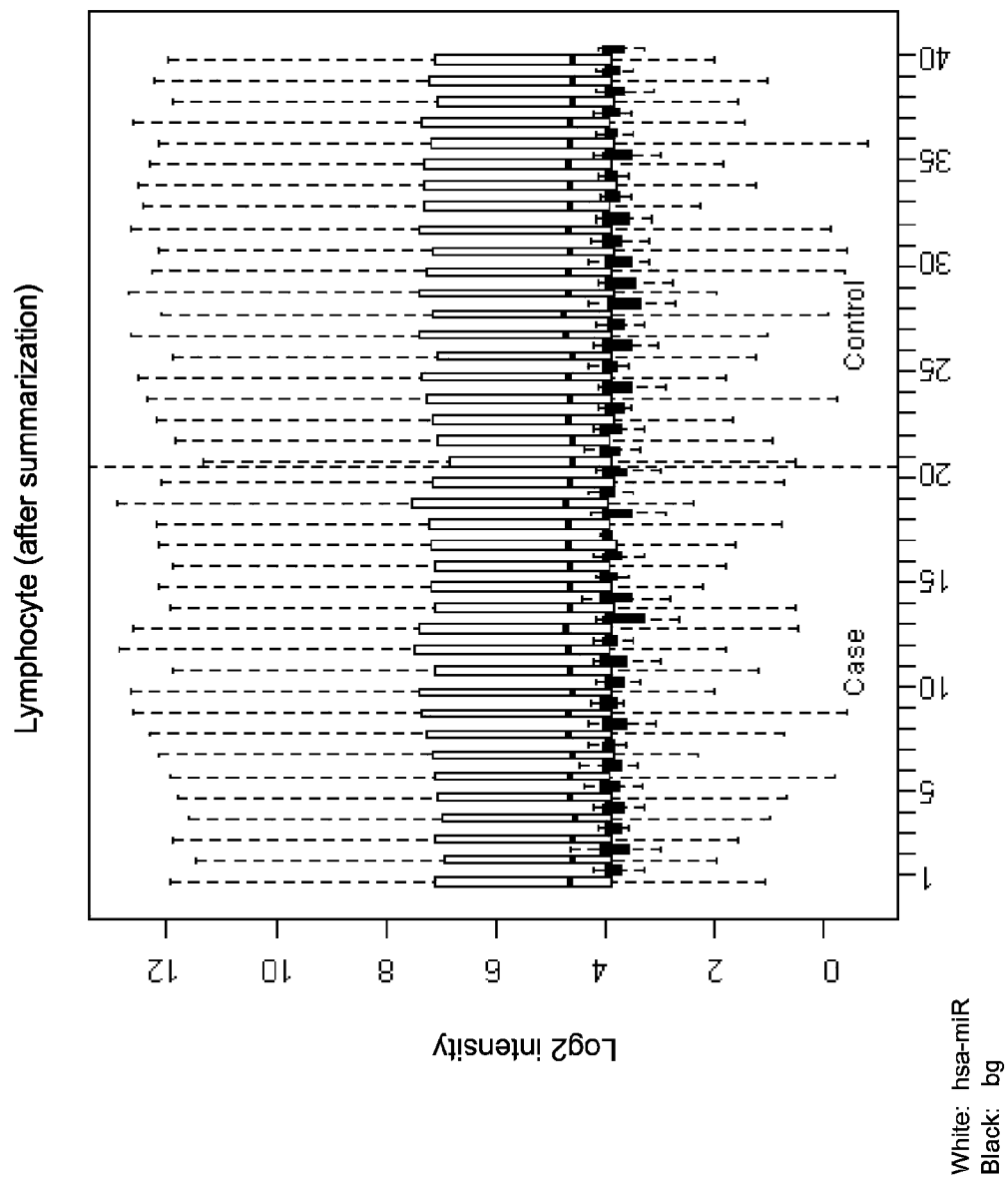
FIG. 6C shows quantile normalized data from the combined platelet and microvesicle fraction.
Figure 7:
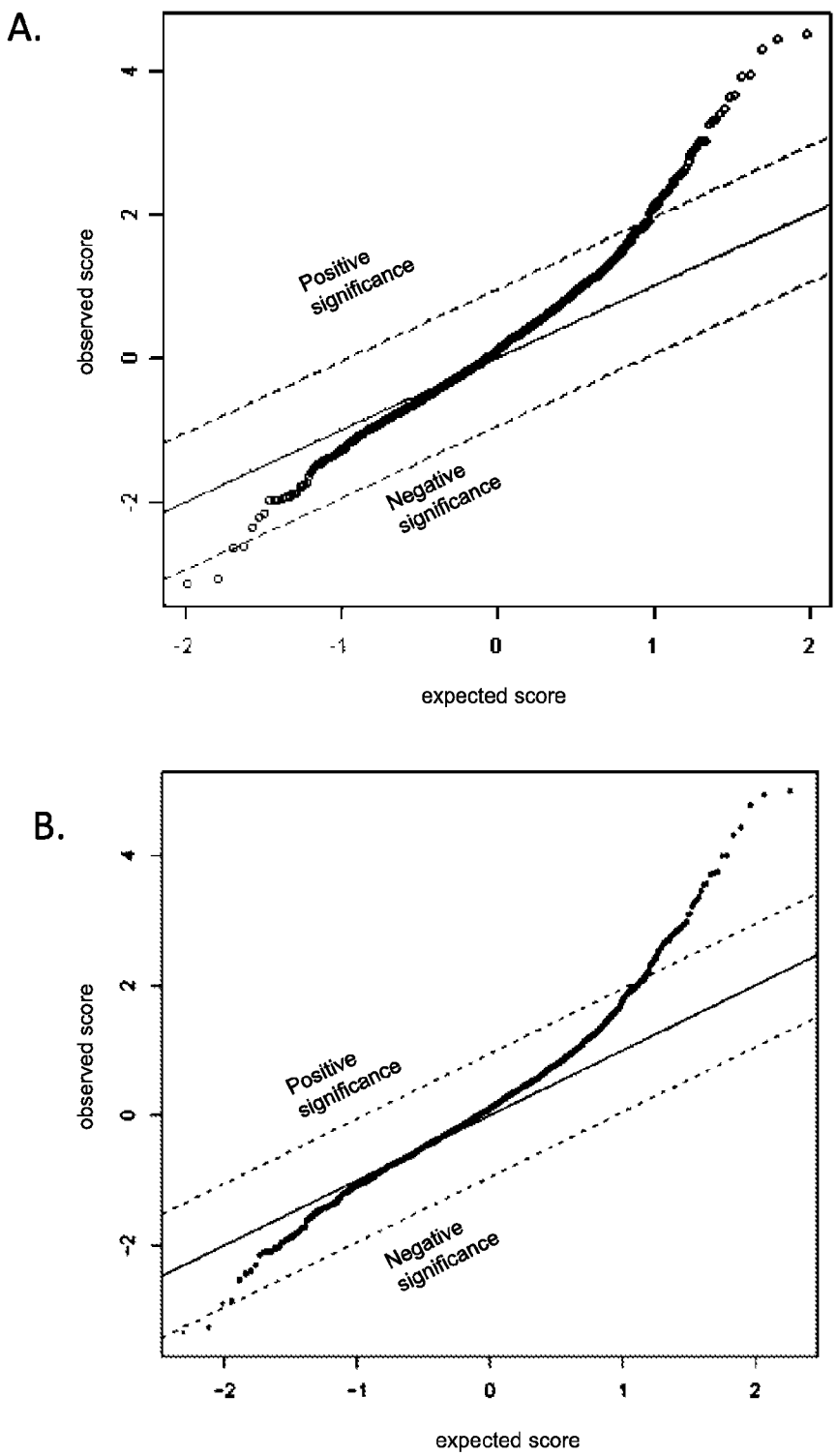
FIG. 7A and FIG. 7B illustrate the SAM analysis of differentially expressed features for the platelet fractions and the platelet+serum microvesicle (Serum) combined fractions, respectively.

Biomarker Derivation from Circulating miRNA Profiles in Different Hematological Fractions We investigated the changes in blood-derived miRNA spectrum in a cohort of ulcerative colitis patients. Blood samples were collected from 20 patients and 20 normal individuals. The case versus control cohorts did not significantly differ by ethnicity, age, gender or familial cancer incidences. A statistically significant disposition to Gastro-intestinal (GI) disorders was found in the patient cohort (8 vs 0 individuals, P=0.0016 by one-sided Fisher exact test) while the control patients demonstrated a greater incidence of non-GI disorders (6 vs 0 individuals, P=0.01 by one-sided Fisher exact test). To enable identification of inflammation-mediated changes the samples were specifically sub-fractionated into PMBC (Peripheral Blood Mononuclear Cells) and platelets. The purity of the isolated fractions was additionally verified by quantitative PCR amplification of either the leukocytic mRNA CD45 or platelet specific gene product Glycoprotein IIB. Additionally, micro-vesicular sub-fractions were isolated to identify markers that were detected free in circulation. Total mRNA from all three sub-fractions was extracted and independently profiled on the Affymetrix miRNA arrays containing 847 human miRNA features. For derivation of miRNA biomarkers that were differentially expressed (DE) each individual hematopoietic fraction was initially analyzed independently. For each analysis, the datasets were split 90:10 with 18 individuals randomly selected from each arm of the study and control cohorts specific to that fraction (FIG. 1). Quantile normalized data from all three fractions (FIGS. 6A, 6B and 6C) were analyzed using Significance Analysis of Microarrays (SAM) and differentially expressed features selected at an FDR threshold of 1% (FIG. 1, FIG. 7A and FIG. 7B). The entire derivation process was repeated 100 times with random re-sampling of the data to minimize the dependency on a single dataset. Finally, the occurrence of the DE features obtained from this iterative process was counted and features demonstrating a frequency greater than 90% selected as potential biomarkers (FIG. 2A). A signature of 31 platelet-derived, 6 microvesicle-derived and 0 PMBC miRNAs were obtained through this process (FIG. 2B).

The 31 platelet-derived miRNAs are listed in Table 1:

TABLE 1

| PLATELET PANEL |
| --- |
| * pl-hsa-let-7i-star_st |
| * pl-hsa-miR-1271_st |

TABLE 1-continued

PLATELET PANEL pl-hsa-miR-1274b__st
* pl-hsa-miR-1296__st
pl-hsa-miR-138__st
pl-hsa-miR-140-3p__st
pl-hsa-miR-143-star__st
pl-hsa-miR-146b-3p__st
pl-hsa-miR-150-star__st
pl-hsa-miR-181b__st
pl-hsa-miR-188-5p__st
pl-hsa-miR-20b-star__st
pl-hsa-miR-22__st
pl-hsa-miR-27a-star__st
* pl-hsa-miR-31__st
pl-hsa-miR-330-3p__st
* pl-hsa-miR-345__st
pl-hsa-miR-362-5p__st
pl-hsa-miR-378__st
pl-hsa-miR-378-star__st
pl-hsa-miR-422a__st
pl-hsa-miR-500__st
pl-hsa-miR-501-5p__st
pl-hsa-miR-532-5p__st
pl-hsa-miR-550-star__st
pl-hsa-miR-720__st
pl-hsa-miR-769-3p__st
pl-hsa-miR-769-5p__st
pl-hsa-miR-874__st
pl-hsa-miR-92a-1-star__st
pl-hsa-miR-941__st

*miRNAs unique to the platelet fraction hsa-miR-941 resides approximately 220 Kb from a high confidence ulcerative colitis susceptibility locus containing rs2297441 that was identified in a genome wide association study. This physical linkage suggests that the miRNA biomarker hsa-miR-941 may be involved in disease susceptibility.

The six serum/microvesicle-derived miRNAs are listed in Table 2:

TABLE 2

MICROVESICLE-DERIVED miRNAs

*sm-hsa-miR-628-5p__st
*sm-hsa-miR-603__st
sm-hsa-miR-202__st
sm-hsa-miR-1263__st
*sm-hsa-miR-221-star__st
*sm-hsa-miR-455-3p__st

*miRNAs unique to the microvesicle fraction

Since no lymphocytic miRNAs were selected through this procedure the entire derivation process was re-run using a union of platelet and microvesicle fractions. A list of 29 biomarkers from this concatenated group was identified and the overlap between the different lists was mapped (FIG. 2B).

The 29 platelet+microvesicle-derived miRNAs are listed in Table 3:

TABLE 3

PLATELET + MICROVESICLE PANEL pl-hsa-miR-1274b__st
pl-hsa-miR-138__st
pl-hsa-miR-140-3p__st
pl-hsa-miR-143-star__st
pl-hsa-miR-146b-3p__st
pl-hsa-miR-150-star__st
pl-hsa-miR-181b__st
pl-hsa-miR-188-5p__st
pl-hsa-miR-20b-star__st
pl-hsa-miR-22__st
pl-hsa-miR-27a-star__st
pl-hsa-miR-330-3p__st
pl-hsa-miR-362-5p__st
pl-hsa-miR-378__st
pl-hsa-miR-378-star__st
pl-hsa-miR-422a__st
*pl-hsa-miR-423-3p__st
pl-hsa-miR-500__st
pl-hsa-miR-501-5p__st
pl-hsa-miR-532-5p__st
pl-hsa-miR-550-star__st
pl-hsa-miR-720__st
pl-hsa-miR-769-3p__st
pl-hsa-miR-769-5p__st
pl-hsa-miR-874__st
pl-hsa-miR-92a-1-star__st
pl-hsa-miR-941__st
*sm-hsa-miR-1263__st
*sm-hsa-miR-202__st

*miRNAs unique to the platelet + microvesicle fraction 89.6% (26/29) of the miRNAs obtained from the combined fraction (derived from platelet and microvesicle) overlapped with biomarkers derived from the platelet fraction only. A subset of only 6 miRNAs were found to be unique between these two datasets with hsa-miR-423-3p exclusive to the platelet-microvesicle combined fraction and hsa-let-7i-star, hsa-miR-1271, hsa-miR-1296, hsa-miR-31 and hsa-miR-345 identified from the platelet derived fraction only. Additionally, 33% (2/6) miRNAs derived from the microvesicle fraction were co-detected with the 2 miRNAs of microvesicle origin in the combined fractions with the exception of hsa-miR-628-5p, hsa-miR-603, hsa-miR-221-star and has-miR-455-3p, which were uniquely detected amongst the 6 microvesicle-specific miRNAs derived from independent analysis of the microvesicle fraction (FIG. 2B). Taken together, this data characterizes two major signatures of differentially expressed miRNA biomarkers of hematopoetic origins in ulcerative colitis—those that are principally derived from the platelet fraction and a minority subset of microvesicular ancestry.

Development and Validation of Recurrence miRNA Predictors

To estimate the predictive capability of these signatures, each of the biomarker categories was subjected to non-probabilistic binary linear classification using Support Vector Machines (SVM) (FIG. 1). Measurement of classifier success was assessed through a 10-fold cross-validation method. A cohort of randomly selected 18 case-control subjects was chosen as the training set while 2 individuals each from the two enrollment categories were reserved for testing. The training set was further stratified to randomly sub-select 16 case-control individuals that were subject to the same feature selection process using SAM originally used in classifier training (FIG. 1). The prediction error rates were then estimated based on application of the SVM classifier to the test set. Through an iterative cycle of 100 repetitions the performance measures (confusion matrix of true positives, true negatives, false positives and false negatives) were computed and recorded. The aggregated summary statistics for the three principal classes (platelets, microvesicle and their union) demonstrated that the best classifier performance was obtained from the 31 miRNAs derived from the platelet fractions, which was capable of classifying patient from control individuals with 92.8% accuracy, 96.2% specificity and 89.5% sensitivity.

The platelet+microvesicle derived class comprising 29 miRNA biomarkers similarly significantly predicted disease outcome with 92.3% accuracy, 96.8% specificity and 87.8% sensitivity. The performance measures of micro-vesicle biomarkers, in contrast, had the least predictive power (62.5% accuracy, 84.8% specificity and 40.3% sensitivity). The performance estimates for these fractions are shown in Tables 4 and 5:

additionally identified that co-clustered based on genomic location i.e hsa-miR-500 and has-miR-501-5p that reside closely on Chr. X and hsa-miR-27a-star and hsa-miR-150-star originating from Chr 19. Co-localization was furthermore observed for one additional candidate miRNA: hsa-mir-769-5p and hsa-mir-769-3p for Cluster 3, while the remaining candidates did not demonstrate positional concordance. In order to independently validate specific candidate biomarkers, a sub category of miRNAs from the platelet derived biomarker panel was pre-selected for verification in enabled quantitative PCR (qPCR) assays. The entire 31

TABLE 4

| Fraction | threshold | Error (%) | FPR (%) | FNR (%) | PPV (%) | NPV (%) | Accuracy | Specificity | Sensitivity |
|---|---|---|---|---|---|---|---|---|---|
| Platelets | 90% | 7.2 | 3.8 | 10.5 | 95.9 | 90.2 | 92.8 | 96.2 | 89.5 |
| Microvesicles | 90% | 37.5 | 15.2 | 59.7 | 72.5 | 58.7 | 62.5 | 84.8 | 40.3 |
| PMBC | 90% | 58 | 55.1 | 60.9 | 41.5 | 42.5 | 42 | 44.9 | 39.1 |
| Combined* | 90% | 8 | 4 | 12 | 95.7 | 88.9 | 92 | 96 | 88 |
| Platelets + Microvescicles | 90% | 7.7 | 3.2 | 12.2 | 96.5 | 88.8 | 92.3 | 96.8 | 87.8 |

TABLE 5

| Fraction | threshold | Error (%) | FPR (%) | FNR (%) | PPV (%) | NPV (%) | Accuracy | Specificity | Sensitivity |
|---|---|---|---|---|---|---|---|---|---|
| Platelets | 100% | 7.6 | 4.5 | 10.6 | 95.2 | 89.9 | 92.4 | 95.5 | 89.4 |
| Microvesicles | 100% | 48.9 | 24.5 | 73.4 | 52.1 | 50.7 | 51.1 | 75.5 | 26.6 |
| PMBC | 100% | 68.8 | 62.5 | 75 | 28.6 | 33.3 | 31.2 | 37.5 | 25 |
| Combined* | 100% | 6.8 | 3.7 | 9.8 | 96.1 | 90.7 | 93.2 | 96.3 | 90.2 |
| Platelets + Microvescicles | 100% | 7.9 | 4.5 | 11.3 | 95.2 | 89.4 | 92.1 | 95.5 | 88.7 |

None of these performance estimates were significantly correlated to independent biometric variables such as age, gender, height or weight though regression analysis. Misclassification estimates from cross-validation revealed that only 4 diseased individuals in the microvesicle-derived category (p14, p15, p18, p21) were misclassified as normals. In contrast these estimates were much more conservative in the platelet-derived or platelet-microvesicle combined classes with, respectively, only 1 (p3) and 0 individuals, being inaccurately classified. These categorization and performance measures thus indicate that the majority of the statistical power in classification of disease versus normal individuals was driven by the platelet derived miRNA biomarker class.

Independent Validation of Levels of Specific Circulating miRNA Biomarkers

Figure 4:
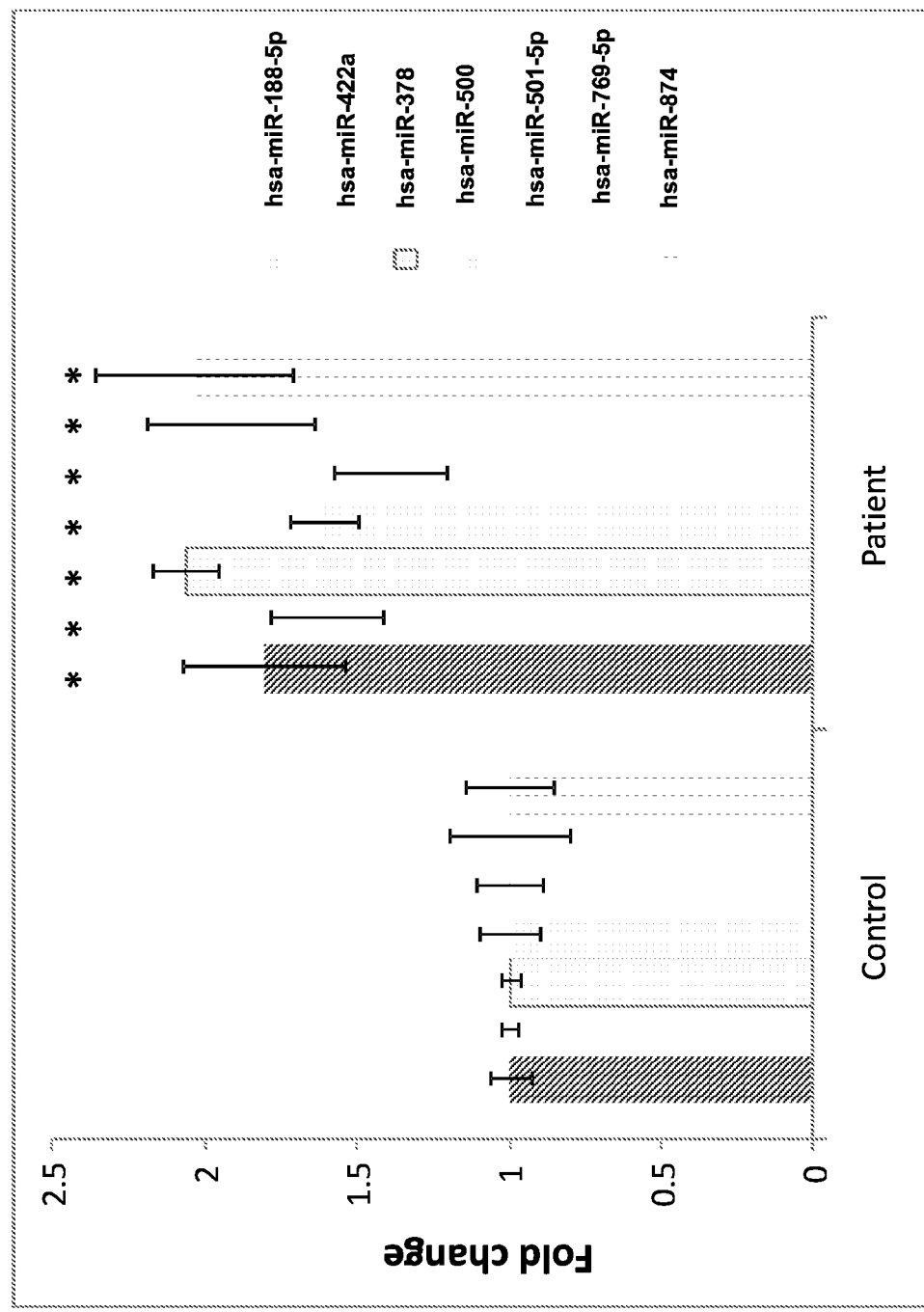
FIG. 4 is a graph illustrating validation of the differentially expressed candidates in a subset of the study panel.

The validity and predictive power of the biomarker panel derived from classifier analysis was evaluated. The differentially expressed profiles of miRNAs derived from the platelet derived biomarker panel demonstrating the highest predictive performance was analyzed through unsupervised hierarchical clustering. The expression map of the 31 candidate miRNAs displayed a clear separation of the patient versus control groups (FIG. 8A) with 3 patients (p3, p19 and p21) being misclassified by the algorithm. The majority of miRNAs in this panel displayed an average log 2 intensity magnitude of >6 with only 22% (7/31) target miRNAs demonstrating lower abundance (normalized log 2 signal intensity <6). Furthermore, correlation among the levels of circulating miRNAs computed through comparison of mean intensity across the patient and control strata revealed a clear separation of 28/31 of the biomarkers into 4 highly correlated clusters with an average correlation coefficient of r=0.75 and p-value of 2.37E-06) (FIG. 3). For one of the 4 largest clusters (Cluster 1) (FIG. 4) miRNA candidates were marker panel was first thresholded at a frequency of 100% and split into 4 quartiles based on p-values, mean intensity and fold changes. A union of all of these categories was taken and eight representative candidate biomarkers, with distributions ranging from marginally below the mean to the maximum intensity measurable on the chip (log 2 intensity values ranging from 7.6 to 13.6) were randomly chosen for validation in pooled platelet samples derived from patient and control cohorts (FIG. 4). The results demonstrated that 88% (7/8) of all the differentially expressed candidates validated successfully in the chosen subset of the study panel and demonstrated a fold change difference ranging from 1.4-2.04 comparing patients over controls (FIG. 4). These estimates matched the array estimates with no significant difference between the two platforms (p-value of 0.6 from two sided Student's t-test). Taken together this data indicates the capability of the selected biomarker panel- to clearly delineate patient and control samples with high degree of confidence. Furthermore this analysis also identifies subsets of miRNAs that demonstrate correlated expression across the samples.

Figure 8B:
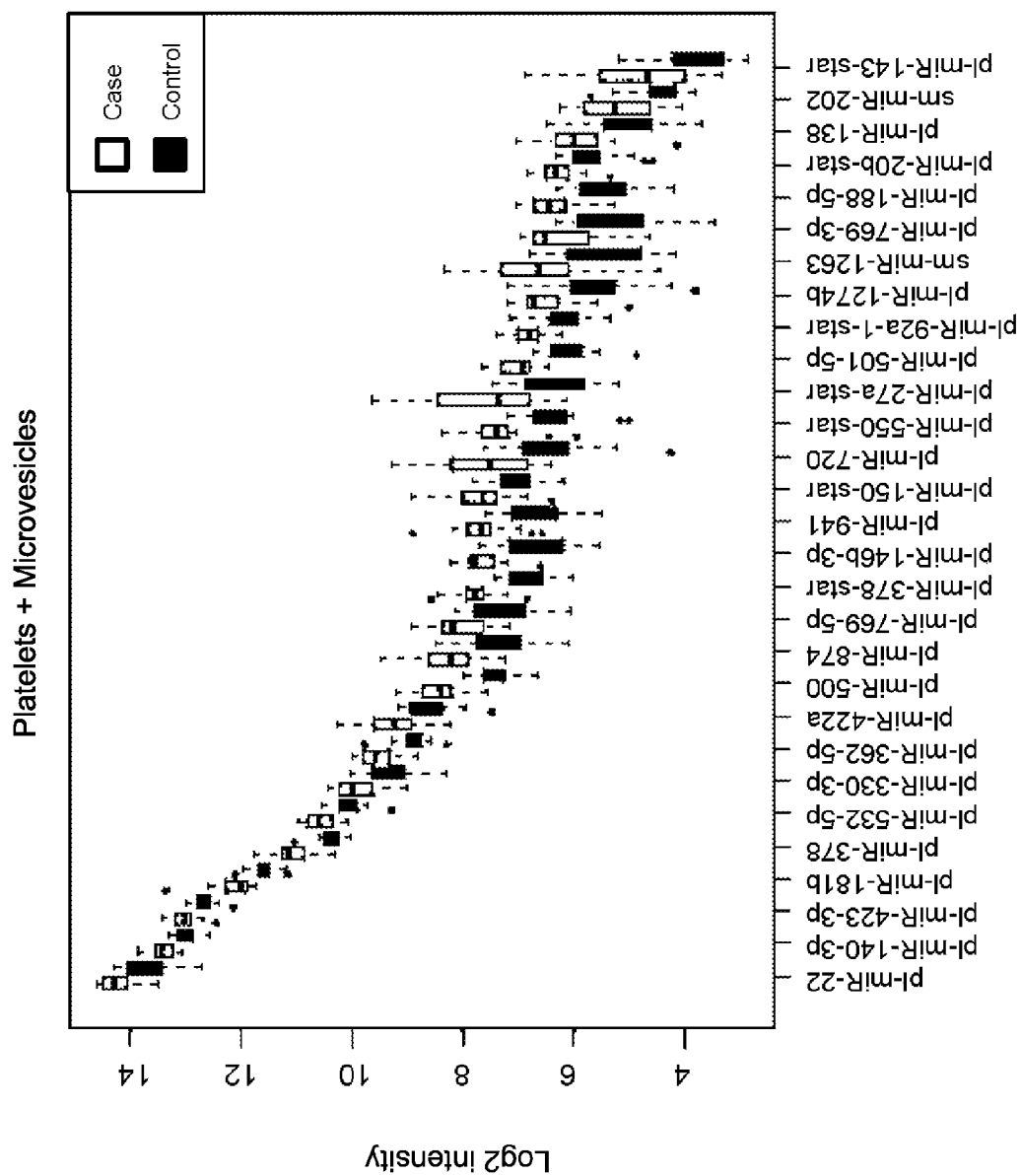
FIG. 8B is a graph illustrating the differentially expressed profiles and relative intensity of case and control samples for the combined platelet and serum microvesicle (serum) fraction.

The differentially expressed profiles of miRNAs derived from the platelet+microvesicle derived biomarker panel demonstrating the highest predictive performance was also analyzed through unsupervised hierarchical clustering. The expression map of the 29 candidate miRNAs is shown in FIG. 8B.

Identification of Gene Pathways Associated with miRNA Biomarker Signatures

To determine the biological significance of the diagnostic signatures, the spectra and response of potential mRNAs targets of the identified biomarkers was evaluated. Predicted targets of the 31 biomarkers were first computationally identified through Target Scan 5.2 and DIANA microT v3.0. A total of 5493 conserved non redundant targets were selected and subjected to Gene Ontology (GO) or Ariadne Ontology and pathway classification using Pathway Studio. Biologically relevant groups were identified by analyzing for significant shared ontology terms. Our analysis revealed that the biomarker targets were significantly enriched in genes associated with transcriptional categories such as transcription factor activity, regulation of transcription nucleotide binding and actin-based cytoskeleton assembly (p-value>$2.74 \times 10^{-10}$), implying a biological role of these miRNAs in the regulation of these processes. Significantly, approximately 27% of the regulated targets (526 genes) were found to be involved in the regulation of transcription and 32% (65 genes) participating in actin-based cytoskeleton assembly. Additionally, analysis of annotated signaling pathways revealed enrichment of pathways that participate in both cytoskeleton regulation and immune-mediated inflammatory response. Specifically, between 24-58% overlap of miRNA targets with genic cascades such as TNF-alpha or T-cell activation pathways known to be involved in triggering the innate immune response was observed. Taken together this data indicates that genic targets of selected diagnostics miRNA biomarkers of Ulcerative Colitis are selectively enriched in candidate genes that engage in hallmark pro-inflammatory response observed in the pathophysiology of this disease.

Correlation of miRNA and mRNA Expression

Figure 5:
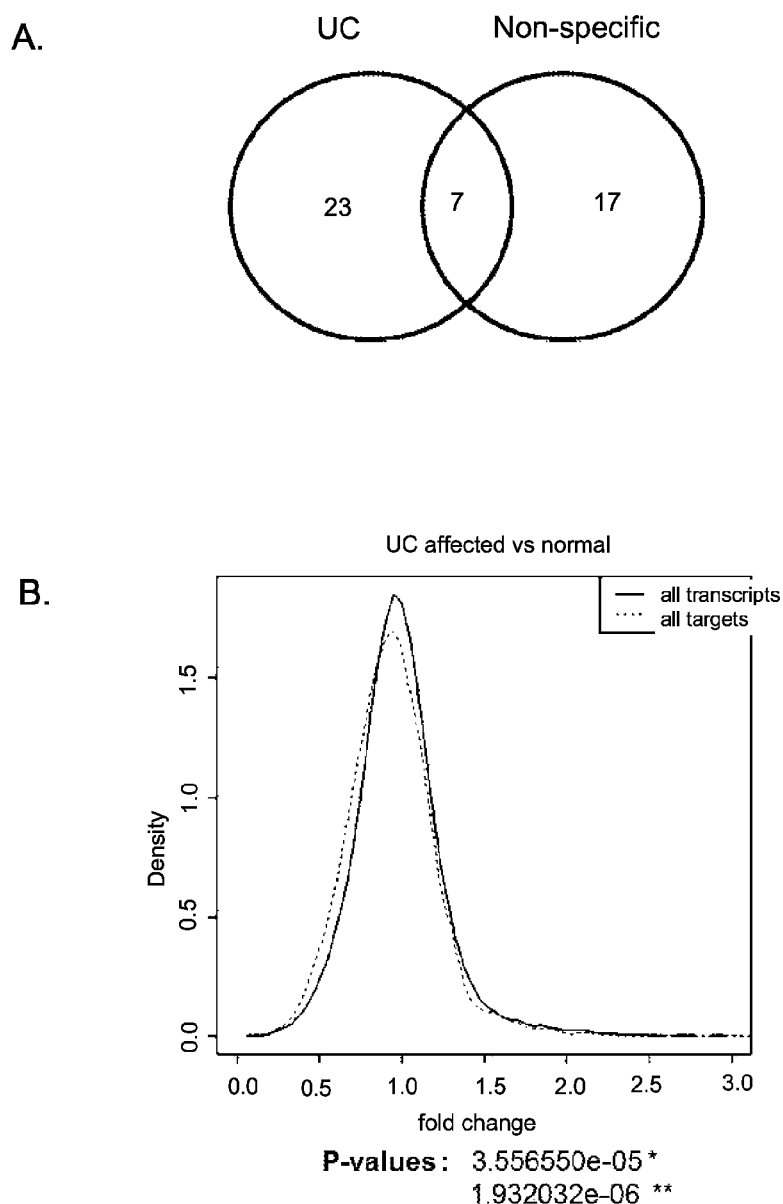
FIG. 5A illustrates overlap between UC-specific and IBD-nonspecific miRNA targets.
FIG. 5B demonstrates the relationship between the fold change densities of miRNA targets and all transcripts profiled from colonic biopsies. The p-values denote significant differences between the two populations by either Bionomial test (*) or by Fisher Exact Test (**).

Given that platelets are a known potent source of inflammatory mediators and actively contribute to local intestinal inflammation, the spectrum of miRNA target genes that are responsive to disease-mediated changes in ulcerative colitis was determined. Since the primary inflammatory response for this disorder is localized in the colon, differentially expressed genes from endoscopic pinch biopsies of the colonic epithelium from normal and diseased patients were investigated. Additionally, gene expression profiles from individuals with bacterial infections were studied in order to explore non-specific inflammatory response from a non-IBD disorder. Differentially expressed gene lists were generated from each of these groups by SAM and a total of 114 non-redundant genes were identified to be significantly changing in the ulcerative colits vs. the normal group. Of this subset, 78% or 89 out of 114 genes demonstrated down-regulation of gene expression. A comparison of this list to miRNA target genes revealed that 34% or 30 out of 89 mRNAs representing the targets of only 17 miRNA biomarkers displayed regulated behavior in the given dataset. This result indicates that a major fraction of the miRNA targets are suppressed at the mRNA level-consistent with the known modes of miRNA:mRNA regulation. By the same principle 35% or 24/68 down-regulated genes were identified as targets of the miRNA biomarkers in the non-specific IBD cohort but with only a 23% overlap (comprised of only 7 common miRNAs) between the UC-specific and IBD-nonspecific miRNA targets (FIG. 5A). This result indicates that not only are specific mRNA regulated conditionally in ulcerative colitis but furthermore that targets of only a subset of the total miRNA biomarkers (57% or 17 out of 30 miRNAs) can potentially mediate disease-induced alterations in a minority of the epithelial mRNA trancriptome. In order to explore this observation globally, the fold change densities of the anti-correlated target mRNAs against all down-regulated transcripts on the array were queried. This analysis revealed a statistically significant difference (p-value of: 0.01100341 by Bionomial test and 0.007436235 by Fisher Exact Test) between the two groups, indicating that the identified panel of miRNA biomarkers can specifically regulate gene expression in a disease specific manner (FIG. 5B). Moreover, based on gene ontology analysis all of the down regulated mRNAs were found to be involved in enriched categories of transcriptional regulation and signal transduction pathways involved in the inflammatory response. Taken together this data demonstrates a biological function of the platelet derived biomarker panel and demonstrates their role in regulating key messages involved in the physiology of ulcerative colitis.

Materials and Methods

Fractionation of Whole Blood into Microvesicle, PMBC and Platelet Fractions and Isolation of RNA Whole blood (7 to 9 ml) was collected from patient and control individuals in BECTON-DICKINSON 16×100 mm 10.0 mL BD Vacutainer® plastic EDTA blood collection Tubes, (Becton & Dickinson, Franklin Lakes, N.J.). To protect against RNA degradation samples were treated with Baker's yeast RNA (Sigma R6750) within 5 minutes of draw to give a final concentration of 1.25 mg/ml and then diluted with equal volume of PBS. Samples were separated into the different hematopoietic fractions by density gradient centrifugation. The diluted blood samples were layered over Ficoll-Paque™ plus (GE Healthcare) at a 3:4 ratio by volume and centrifuged at 400 g for 30 to 40 minutes at 25° C. This process resulted in a fractionation into plasma (upper layer), PMBCs and platelets (narrow central band), and a band of erythrocytes and granulocytes at the tube bottom. The upper plasma layer was removed, centrifuged at 100,000 g for 1 hr at 4° C. using a Beckman TI 50 rotor and the pellet isolated to generate the micro-vesicular fraction. To fractionate the PMBC from Platelets, the Ficoll-Paque layer containing these cellular populations was removed, 3 volumes of 1×PBS was added to the layer and the mixture was centrifuged at 65 g for 15 min at room temperature. The supernatant fraction was saved and the pellet re-suspended in 10 ml PBS and re-centrifuged under the same conditions. The resulting pellet was isolated to represent the high density PMBC population. The supernatant fractions from the first and second washes were pooled and centrifuged at 450 g for 20 min at room temperature to isolate the pellet representing the platelet fraction. All three pellet fractions representing were mixed with 1 ml of Trizol-LS reagent and total RNA extracted according to the Trizol procedure. Low molecular weight RNAs were isolated by Microcon YM-100 columns (Millipore) and concentrated with Microcon YM-3 columns (Millipore). Isolated RNA was quantitated with the Quant-iT RiboGreen RNA Assay Kit (Invitrogen).

Labeling and Hybridization of Platelet, Microvesicle and Lymphocytic Samples to the Affymetrix miRNA Arrays Total RNA ranging in concentration from 1 µg-3 µg were labeled using the Genisphere HSR labeling kit (P/N HSR30FTA) and hybridized overnight to the Affymetrix Genechip miRNA array (P/N 901326). The arrays were washed and stained using standard Affymetrix protocols and scanned using the Affymetrix GCS 3000 7G Scanner. Feature intensities were extracted using the miRNA_1-0_2xgain library files.

Quantitative RT-PCR

Assays to quantify differential expression of miRNAs in patients vs. healthy controls were performed using the ABI 7300 real-time PCR instrument and miScript quantitative PCR System (Qiagen). Pooled Patient (P2-P21) and Control (C1-C18 and C20) samples were used in duplicate Reverse Transcription (RT) reactions. Approximately, 10 ng of cDNA were used in duplicate PCR assays for each RT. The normalizers used for this analysis were: Hs_RNU6B_3, Hs_miR-320b_2, Hs_miR-543_1 and Hs_miR-654-3p_2. Oligonucleotide sets were purchased from Qiagen.

Datasets

The datasets described in this manuscript are MIAME compliant and have been deposited in NCBI's Gene Expression Omnibus Database (ncbi.nlm.nih.gov/geo/). The data series is accessible through GEO Series accession number GSE32273.

Analysis of the miRNA Data

Data Preprocessing

Data preprocessing was performed via Affymetrix miRNA QC Tool, which consisted of extraction of raw intensities for each individual feature followed by background subtraction based on GC content of anti-genomic probes, transformation of values through addition of a small constant (value 16), quantile normalization and finally median summarization of all probe sets for each feature. The intensity data used in all analysis were log 2 transformed. Furthermore, triplicates available for one case (p7) and one control (c9) for each of the fractions under study were analyzed by utilizing the mean intensity values.

Software Packages

All statistical analysis was performed under the R programming language and environment (r-project.org). The R "samr" package was used for significance analysis for microarray (SAM) and the R "e1071" package was used for support vector machine (SVM) with the non-linear radial basis function as the kernel. The unsupervised Hierarchical clustering algorithm in the R "hclust" function was generated using the Euclidean distance matrix and complete-linkage agglomeration. All heat maps were generated by the R "gplots" package.

miRNA Biomarker Selection

Biomarker selection was based on 100 iterative cycles of SAM run on re-sampling of the full 20 patient and 20 control sample set through a randomized 9:1 data split (i.e a "training set" of 18 cases and 18 control individual per iteration). Each individual fraction (platelet, microvesicle or PMBCs), or the combination of all three fractions were separately analyzed. Differentially expressed (DE) miRNA features were identified at a False Discovery Rate of 1% and features occurring at a frequency greater than 90% (consensus features) selected as potential biomarkers.

Cross-Validation to Estimate Prediction Error Rates

Support Vector Machines (SVM) were used for classifying the IBD cases from controls. To assess the prediction error rates, a 10-fold cross-validation procedure on the consensus features was utilized. Briefly, the training set was split into a random subset of 16 cases/controls and the biomarker derivation process run iteratively through SAM to select the consensus features followed by SVM classification. The prediction error rates for classifier success was then computed from the remaining 2 cases/controls individuals through generation of a confusion matrix (e.g., false positives and false negatives). The entire classification algorithm was repeated 100 times to estimate the aggregated prediction error rates.

Inter-Feature Correlation Analysis Among the 31 Biomarkers

The correlation structure among the 31 biomarkers derived from the platelet fraction was examined by calculating the Pearson's correlation coefficients among the 31 biomarkers based on their mean expression profiles across cases and control individuals. Clusters with minimal correlation coefficients >0.6 were identified by visualizing the heat map plotted by unsupervised hierarchical clustering.

Prediction of miRNA Targets and Enrichment Analysis

For prediction of mRNA targets, the 31 platelet derived biomarkers were first separated into two categories based on the star designation. Targets were determined using either the DIANA-microT 3.0 algorithm for the star miRNA sequences (diana.cslab.ece.ntua.gr/) and TargetScan Human v5.0 (targetscan.org) for the non-star miRNA sequences. Targets were selected based on conservation of families/sites from Target Scan and a precision score greater than 0.4 from DIANA. A total of 5493 unique mRNAs were selected after removing redundancies and subjected to pathway exploration using Pathway Studio software from Ariadne Genomics (ariadnegenomics.com). Using this software and its accompanying Gene Ontology and interaction database, incidence of predicted miRNA targets were matched against the target collection and the top-ranking pathways and Gene Ontology groups selected. The statistical enrichment for each of these pathways/groups were computed by the similarity score or p-value calculated as a ratio of a number of common objects between two pathways to the total number of objects in them. The percentage of overlap and the overlapping entities of the top 25 groups/pathways ranked by most significant p-values are listed in Table S6.

Correlation Analysis of miRNA and mRNA Expressions

To identify expression changes in putative target mRNAs, genome-wide mRNA expression data from colonic pinch biopsies of ulcerative colitis patients were analyzed (Wu et al. 2007). The pre-processed raw intensities for 12,258 probes (excluding the control probes from the array) were extracted from patient control cohorts (4 normals, 5 affected ulcerative colitis and 2 non-IBD patients as controls). Differentially expressed mRNAs were identified by SAM at an FDR<0.1% and genes exhibiting a fold change >2 selected for further analysis. The number of differentially expressed genes was counted for both the whole array and the miRNA targets and enrichment of down-regulated target mRNAs assessed by either the Binomial test or the Fisher's Exact test.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method for detecting differential expression of miRNA in a human subject comprising:
   a) hybridizing miRNAs isolated from a platelet fraction of blood to complementary oligonucleotides, wherein the isolated miRNAs include a panel of miRNA biomarkers consisting of pl-hsa-let-7i-star_st, pl-hsa-miR-1271_st, pl-hsa-miR-1274b_st, pl-hsa-miR-1296_st, pl-hsa-miR-138_st, pl-hsa-miR-140-3p_st, pl-hsa-miR-143-star_st, pl-hsa-miR-146b-3p_st, pl-hsa-miR-150-star_st, pl-hsa-miR-181b_st, pl-hsa-miR-188-5p_st, pl-hsa-miR-20b-star_st, pl-hsa-miR-22_st, pl-hsa-miR-27a-star_st, pl-hsa-miR-31_st, pl-hsa-miR-330-3p_st, pl-hsa-miR-345_st, pl-hsa-miR-362-5p_st, pl-hsa-miR-378_st, pl-hsa-miR-378-star_st, pl-hsa-miR-422a_st, pl-hsa-miR-500_st, pl-hsa-miR-501-5p_st, pl-hsa-miR-532-5p_st, pl-hsa-miR-550-star_st, pl-hsa-miR-720_st, pl-hsa-miR-769-3p_st, pl-hsa-miR-769-5p_st, pl-hsa-miR-874_st, pl-hsa-miR-92a-1-star_st, and pl-hsa-miR-941_st, and wherein the complementary oligonucleotides consist of oligonucleotides complementary to the panel of miRNA biomarkers;

b) quantifying hybridization of each of the miRNA biomarkers to the complementary oligonucleotides; and c) detecting an increase in expression of at least 1.4-fold in each of the miRNA biomarkers compared to normal expression levels of the miRNA biomarkers.

2. The method of claim 1, wherein the miRNAs are quantified using a detection method wherein the miRNA complementary oligonucleotides are attached to a solid surface.

3. The method of claim 2, wherein the oligonucleotides complementary to the panel of miRNA biomarkers are complementary features on a microarray.

4. The method of claim 3, wherein the microarray further comprises
normalization controls.

5. The method of claim 3, wherein hybridization is quantitated by measurement of fluorescence intensity.

6. The method of claim 1, wherein an increase in expression of 1.4-2.04-fold in each of the miRNAs compared to normal expression levels is detected.

* * * * *